(12) United States Patent
Todd

(10) Patent No.: US 12,232,732 B2
(45) Date of Patent: Feb. 25, 2025

(54) ANASTOMOSIS DEVICES

(71) Applicant: W. L. Gore & Associates, Inc., Newark, DE (US)

(72) Inventor: Daniel H. Todd, North East, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 23 days.

(21) Appl. No.: 18/104,993

(22) Filed: Feb. 2, 2023

(65) Prior Publication Data

US 2023/0255632 A1 Aug. 17, 2023

Related U.S. Application Data

(63) Continuation of application No. 17/039,569, filed on Sep. 30, 2020, now Pat. No. 11,596,409, which is a
(Continued)

(51) Int. Cl.
| | | |
|---|---|---|
| *A61B 17/11* | (2006.01) | |
| *A61B 17/00* | (2006.01) | |
| *A61F 2/06* | (2013.01) | |
| *A61F 2/90* | (2013.01) | |
| *A61B 17/064* | (2006.01) | |

(Continued)

(52) U.S. Cl.
CPC ...... *A61B 17/1114* (2013.01); *A61B 17/0057* (2013.01); *A61B 17/11* (2013.01); *A61F 2/06* (2013.01); *A61F 2/90* (2013.01); *A61B 17/064* (2013.01); *A61B 2017/0641* (2013.01); *A61B 17/08* (2013.01); *A61B 17/083* (2013.01); *A61B 2017/1103* (2013.01); *A61B 2017/1107* (2013.01); *A61B 2017/1132* (2013.01); *A61B 2017/1135* (2013.01); *A61B 2017/1139* (2013.01); *A61F 2002/077* (2013.01)

(58) Field of Classification Search
CPC . A61B 17/1114; A61B 17/0057; A61B 17/11; A61B 17/064; A61B 17/08; A61B 17/083; A61B 2017/0641; A61B 2017/1107; A61B 2017/1132
See application file for complete search history.

(56) References Cited

U.S. PATENT DOCUMENTS

| | | | |
|---|---|---|---|
| 3,818,511 A | 6/1974 | Goldberg et al. | |
| 4,119,100 A | 10/1978 | Rickett | |

(Continued)

FOREIGN PATENT DOCUMENTS

| | | |
|---|---|---|
| CN | 201379668 Y | 1/2010 |
| CN | 101951983 A | 1/2011 |

(Continued)

OTHER PUBLICATIONS

International Search Report from PCT/US2015/028717, mailed Aug. 26, 13 pages.

*Primary Examiner* — Phong Son H Dang

(57) ABSTRACT

Implantable medical devices for connecting tissue layers or occluding body conduits and tissue structures include apposition portions, a central region, and a covering material. The methods of using the devices include endoscopic deployment, and the devices may include self-expanding frameworks that facilitate a secure connection between the tissue structures. In some embodiments, one or more tethers are used to longitudinally contract the device in situ.

18 Claims, 5 Drawing Sheets

Related U.S. Application Data continuation of application No. 15/969,038, filed on May 2, 2018, now Pat. No. 10,806,458, which is a continuation of application No. 14/700,480, filed on Apr. 30, 2015, now Pat. No. 10,004,509.

(60) Provisional application No. 61/987,954, filed on May 2, 2014.

(51) Int. Cl.
*A61B 17/08* (2006.01)
*A61F 2/07* (2013.01)

(56) References Cited

U.S. PATENT DOCUMENTS

| | | |
|---|---|---|
| 4,338,937 A | 7/1982 | Lerman |
| 4,381,765 A | 5/1983 | Burton |
| 5,171,259 A | 12/1992 | Inoue |
| 5,224,953 A | 7/1993 | Morgentaler |
| 5,261,898 A | 11/1993 | Polin et al. |
| 5,354,308 A | 10/1994 | Simon et al. |
| 5,562,728 A | 10/1996 | Lazarus et al. |
| 5,741,297 A | 4/1998 | Simon |
| 5,755,778 A | 5/1998 | Kleshinski |
| 5,797,933 A | 8/1998 | Snow et al. |
| 5,824,041 A | 10/1998 | Lenker et al. |
| 5,830,222 A | 11/1998 | Makower |
| 5,868,783 A | 2/1999 | Tower |
| 5,945,994 A | 8/1999 | Shimizu et al. |
| 5,957,949 A | 9/1999 | Leonhardt et al. |
| 6,007,544 A | 12/1999 | Kim |
| 6,077,291 A | 6/2000 | Das |
| 6,120,534 A | 9/2000 | Ruiz |
| 6,165,209 A | 12/2000 | Patterson et al. |
| 6,168,621 B1 | 1/2001 | Vrba |
| 6,171,329 B1 | 1/2001 | Shaw et al. |
| 6,193,734 B1 | 2/2001 | Bolduc et al. |
| 6,214,029 B1 | 4/2001 | Thill et al. |
| 6,217,608 B1 | 4/2001 | Penn et al. |
| 6,290,728 B1 | 9/2001 | Phelps et al. |
| 6,315,708 B1 | 11/2001 | Salmon et al. |
| 6,315,792 B1 | 11/2001 | Armstrong et al. |
| 6,355,052 B1 | 3/2002 | Neuss et al. |
| 6,391,036 B1 | 5/2002 | Berg et al. |
| 6,391,039 B1 | 5/2002 | Nicholas et al. |
| 6,416,543 B1 | 7/2002 | Hilaire et al. |
| 6,419,681 B1 | 7/2002 | Vargas et al. |
| 6,432,127 B1 | 8/2002 | Kim et al. |
| 6,468,303 B1 | 10/2002 | Amplatz et al. |
| 6,485,496 B1 | 11/2002 | Suyker et al. |
| 6,485,507 B1 | 11/2002 | Walak et al. |
| 6,488,702 B1 | 12/2002 | Besselink |
| 6,579,314 B1 | 6/2003 | Lombardi et al. |
| 6,585,758 B1 | 7/2003 | Chouinard et al. |
| 6,616,675 B1 | 9/2003 | Evard et al. |
| 6,629,992 B2 | 10/2003 | Bigus et al. |
| 6,666,883 B1 | 12/2003 | Seguin et al. |
| 6,712,836 B1 | 3/2004 | Berg et al. |
| 6,863,684 B2 | 3/2005 | Kim et al. |
| 6,866,674 B2 | 3/2005 | Galdonik et al. |
| 6,911,037 B2 | 6/2005 | Gainor et al. |
| 6,945,994 B2 | 9/2005 | Austin et al. |
| 6,958,037 B2 | 10/2005 | Ewers et al. |
| 7,022,131 B1 | 4/2006 | Derowe et al. |
| 7,025,777 B2 | 4/2006 | Moore |
| 7,029,482 B1 | 4/2006 | Vargas et al. |
| 7,037,344 B2 | 5/2006 | Kagan et al. |
| 7,115,136 B2 | 10/2006 | Park et al. |
| 7,182,771 B1 | 2/2007 | Houser et al. |
| 7,223,274 B2 | 5/2007 | Vargas et al. |
| 7,252,680 B2 | 8/2007 | Freitag |
| 7,303,569 B2 | 12/2007 | Yencho et al. |
| 7,431,729 B2 | 10/2008 | Chanduszko |
| 7,527,644 B2 | 5/2009 | Mangiardi et al. |
| 7,547,321 B2 | 6/2009 | Silvestri et al. |
| 7,585,306 B2 | 9/2009 | Abbott et al. |
| 7,608,086 B2 | 10/2009 | Tanaka et al. |
| 7,632,302 B2 | 12/2009 | Vreeman et al. |
| 7,780,686 B2 | 8/2010 | Park et al. |
| 7,828,814 B2 | 11/2010 | Brenneman et al. |
| 7,892,247 B2 | 2/2011 | Conston et al. |
| 7,901,430 B2 | 3/2011 | Matsuura et al. |
| 8,029,534 B2 | 10/2011 | Hruska et al. |
| 8,043,360 B2 | 10/2011 | McNamara et al. |
| 8,109,946 B2 | 2/2012 | Cahill et al. |
| 8,114,125 B2 | 2/2012 | Seibold et al. |
| 8,197,498 B2 | 6/2012 | Coleman et al. |
| 8,257,389 B2 | 9/2012 | Chanduszko et al. |
| 8,262,691 B2 | 9/2012 | McGuckin et al. |
| 8,343,088 B2 | 1/2013 | Bates et al. |
| 8,398,676 B2 | 3/2013 | Roorda et al. |
| 8,409,167 B2 | 4/2013 | Roschak |
| 8,425,539 B2 | 4/2013 | Binmoeller et al. |
| 8,430,934 B2 | 4/2013 | Das |
| 8,435,284 B2 | 5/2013 | Eidenschink et al. |
| 8,454,632 B2 | 6/2013 | Binmoeller et al. |
| 8,579,935 B2 | 11/2013 | Devries et al. |
| 8,641,747 B2 | 2/2014 | Brenneman et al. |
| 8,679,171 B2 | 3/2014 | Deem et al. |
| 8,728,155 B2 | 5/2014 | Montorfano et al. |
| 8,740,940 B2 | 6/2014 | Maahs et al. |
| 8,864,813 B2 | 10/2014 | Barr |
| 8,870,916 B2 | 10/2014 | Ewers et al. |
| 8,992,604 B2 | 3/2015 | Gross et al. |
| 9,597,204 B2 | 3/2017 | Benary et al. |
| 9,668,853 B2 | 6/2017 | Shin |
| 9,782,533 B2 | 10/2017 | Brenneman et al. |
| 9,993,251 B2 | 6/2018 | Todd et al. |
| 10,004,509 B2 | 6/2018 | Todd |
| 10,363,040 B2 | 7/2019 | Sambandam |
| 10,806,458 B2 | 10/2020 | Todd |
| 11,439,396 B2 | 9/2022 | Johnson et al. |
| 11,596,409 B2 | 3/2023 | Todd |
| 11,980,367 B2 | 5/2024 | Houghton et al. |
| 2001/0021872 A1 | 9/2001 | Bailey et al. |
| 2001/0047180 A1 | 11/2001 | Grudem et al. |
| 2002/0082627 A1 | 6/2002 | Berg et al. |
| 2002/0099431 A1 | 7/2002 | Armstrong et al. |
| 2002/0099437 A1 | 7/2002 | Anson et al. |
| 2002/0161341 A1 | 10/2002 | Stinson et al. |
| 2002/0169475 A1 | 11/2002 | Gainor et al. |
| 2002/0183787 A1 | 12/2002 | Wahr et al. |
| 2003/0028213 A1 | 2/2003 | Thill et al. |
| 2003/0032967 A1 | 2/2003 | Park et al. |
| 2003/0055441 A1 | 3/2003 | Suyker et al. |
| 2003/0069533 A1 | 4/2003 | Kakutani et al. |
| 2003/0109893 A1 | 6/2003 | Vargas et al. |
| 2003/0120292 A1 | 6/2003 | Park et al. |
| 2003/0139819 A1 | 7/2003 | Beer et al. |
| 2003/0144578 A1 | 7/2003 | Koster |
| 2003/0191482 A1 | 10/2003 | Suyker et al. |
| 2004/0073242 A1 | 4/2004 | Chanduszko |
| 2004/0078053 A1 | 4/2004 | Berg et al. |
| 2004/0092977 A1 | 5/2004 | Vargas et al. |
| 2004/0098105 A1 | 5/2004 | Stinson et al. |
| 2004/0133236 A1 | 7/2004 | Chanduszko |
| 2004/0204755 A1 | 10/2004 | Robin |
| 2004/0211433 A1 | 10/2004 | Albright |
| 2005/0049675 A1 | 3/2005 | Wallace |
| 2005/0055082 A1 | 3/2005 | Ben et al. |
| 2005/0070934 A1 | 3/2005 | Tanaka et al. |
| 2005/0070935 A1 | 3/2005 | Ortiz |
| 2005/0070957 A1 | 3/2005 | Das |
| 2005/0149071 A1 | 7/2005 | Abbott et al. |
| 2005/0154465 A1 | 7/2005 | Hodges et al. |
| 2005/0228413 A1 | 10/2005 | Binmoeller et al. |
| 2005/0234509 A1 | 10/2005 | Widomski et al. |
| 2005/0251201 A1 | 11/2005 | Roue et al. |
| 2005/0273124 A1 | 12/2005 | Chanduszko |
| 2005/0288786 A1 | 12/2005 | Chanduszko |
| 2006/0047337 A1 | 3/2006 | Brenneman |
| 2006/0052821 A1 | 3/2006 | Abbott et al. |
| 2006/0106418 A1 | 5/2006 | Seibold et al. |

(56) References Cited

U.S. PATENT DOCUMENTS

| | | |
|---|---|---|
| 2006/0200228 A1 | 9/2006 | Penn et al. |
| 2006/0212055 A1 | 9/2006 | Karabey et al. |
| 2006/0217761 A1 | 9/2006 | Opolski |
| 2007/0055358 A1 | 3/2007 | Krolik et al. |
| 2007/0073337 A1 | 3/2007 | Abbott et al. |
| 2007/0123917 A1 | 5/2007 | Ortiz et al. |
| 2007/0168014 A1 | 7/2007 | Jimenez et al. |
| 2007/0244518 A1 | 10/2007 | Callaghan |
| 2007/0249985 A1 | 10/2007 | Brenneman et al. |
| 2007/0250153 A1* | 10/2007 | Cully ............... A61F 2/07 623/1.13 |
| 2007/0282430 A1 | 12/2007 | Thommen et al. |
| 2007/0283552 A1 | 12/2007 | Gale et al. |
| 2008/0086168 A1 | 4/2008 | Cahill |
| 2008/0091235 A1 | 4/2008 | Sirota |
| 2008/0243151 A1 | 10/2008 | Binmoeller et al. |
| 2008/0262518 A1 | 10/2008 | Freudenthal |
| 2009/0076541 A1 | 3/2009 | Chin et al. |
| 2009/0090366 A1 | 4/2009 | Cuevas et al. |
| 2009/0093873 A1 | 4/2009 | Navia |
| 2009/0143713 A1 | 6/2009 | Van et al. |
| 2009/0187240 A1 | 7/2009 | Clerc et al. |
| 2009/0216265 A1* | 8/2009 | DeVries ............ A61B 17/068 606/213 |
| 2009/0228038 A1 | 9/2009 | Amin |
| 2009/0240316 A1* | 9/2009 | Bruszewski ......... A61F 2/07 623/1.13 |
| 2009/0270971 A1* | 10/2009 | Xiao ................. A61F 2/07 623/1.13 |
| 2009/0281557 A1 | 11/2009 | Sander et al. |
| 2010/0010520 A1 | 1/2010 | Takahashi et al. |
| 2010/0023132 A1 | 1/2010 | Imran |
| 2010/0036401 A1 | 2/2010 | Navia |
| 2010/0100105 A1 | 4/2010 | Bates et al. |
| 2010/0106171 A1 | 4/2010 | Arepally et al. |
| 2010/0114128 A1 | 5/2010 | Coleman et al. |
| 2010/0114290 A1 | 5/2010 | Rasmussen et al. |
| 2010/0130995 A1 | 5/2010 | Yevzlin et al. |
| 2010/0174253 A1 | 7/2010 | Cline et al. |
| 2010/0234878 A1 | 9/2010 | Hruska et al. |
| 2010/0256548 A1 | 10/2010 | McNamara et al. |
| 2010/0268316 A1 | 10/2010 | Brenneman et al. |
| 2010/0305590 A1 | 12/2010 | Holmes et al. |
| 2011/0040366 A1 | 2/2011 | Goetz et al. |
| 2011/0054381 A1 | 3/2011 | Van et al. |
| 2011/0060398 A1 | 3/2011 | Tupil et al. |
| 2011/0118765 A1 | 5/2011 | Aguirre |
| 2011/0125244 A1 | 5/2011 | Roeder et al. |
| 2011/0137410 A1 | 6/2011 | Hacohen |
| 2011/0213415 A1 | 9/2011 | McGuckin et al. |
| 2011/0218609 A1 | 9/2011 | Chobotov et al. |
| 2011/0257461 A1 | 10/2011 | Lipperman et al. |
| 2011/0257723 A1 | 10/2011 | McNamara |
| 2011/0301689 A1 | 12/2011 | Dorn et al. |
| 2012/0065652 A1 | 3/2012 | Cully et al. |
| 2012/0089216 A1 | 4/2012 | Rapaport et al. |
| 2012/0130417 A1 | 5/2012 | Lepulu et al. |
| 2012/0172927 A1 | 7/2012 | Campbell et al. |
| 2012/0232505 A1 | 9/2012 | Eskaros et al. |
| 2012/0283811 A1* | 11/2012 | Neilan ............... A61F 2/07 623/1.2 |
| 2013/0012969 A1 | 1/2013 | Shin |
| 2013/0030351 A1 | 1/2013 | Belhe et al. |
| 2013/0030521 A1 | 1/2013 | Nitzan et al. |
| 2013/0041451 A1 | 2/2013 | Patterson et al. |
| 2013/0053784 A1 | 2/2013 | Houser et al. |
| 2013/0096606 A1 | 4/2013 | Bruchman et al. |
| 2013/0165967 A1 | 6/2013 | Amin et al. |
| 2013/0197623 A1 | 8/2013 | McHugo |
| 2013/0218192 A1 | 8/2013 | Erzberger et al. |
| 2013/0245742 A1 | 9/2013 | Norris |
| 2013/0261531 A1 | 10/2013 | Gallagher et al. |
| 2013/0317546 A1 | 11/2013 | Brown |
| 2014/0012368 A1 | 1/2014 | Sugimoto et al. |
| 2014/0031842 A1 | 1/2014 | Brenneman et al. |
| 2014/0074155 A1 | 3/2014 | Rothstein et al. |
| 2014/0236064 A1 | 8/2014 | Binmoeller et al. |
| 2014/0303710 A1 | 10/2014 | Zhang et al. |
| 2014/0343602 A1 | 11/2014 | Cox et al. |
| 2015/0005810 A1 | 1/2015 | Center et al. |
| 2015/0066077 A1 | 3/2015 | Akpinar |
| 2015/0250630 A1 | 9/2015 | Irwin et al. |
| 2015/0265437 A1 | 9/2015 | Fleury et al. |
| 2015/0313595 A1 | 11/2015 | Houghton et al. |
| 2015/0313598 A1 | 11/2015 | Todd et al. |
| 2015/0313599 A1 | 11/2015 | Johnson et al. |
| 2016/0045199 A1 | 2/2016 | Mooney |
| 2016/0074023 A1 | 3/2016 | Sakamoto et al. |
| 2016/0135813 A1 | 5/2016 | Johnson et al. |
| 2016/0256251 A1 | 9/2016 | Ben-Muvhar et al. |
| 2017/0020498 A1 | 1/2017 | Blom |
| 2017/0105854 A1 | 4/2017 | Treacy et al. |
| 2018/0221194 A1 | 8/2018 | Eskaros et al. |
| 2018/0242972 A1 | 8/2018 | Todd |
| 2018/0250009 A1 | 9/2018 | Todd et al. |
| 2018/0296809 A1 | 10/2018 | Johnson |
| 2020/0015823 A1 | 1/2020 | Sambandam |
| 2020/0146680 A1 | 5/2020 | Houghton et al. |
| 2021/0085328 A1 | 3/2021 | Todd |
| 2022/0257252 A1 | 8/2022 | Todd et al. |
| 2022/0370071 A1 | 11/2022 | Johnson et al. |

FOREIGN PATENT DOCUMENTS

| | | |
|---|---|---|
| CN | 102083391 A | 6/2011 |
| CN | 102395323 A | 3/2012 |
| CN | 102802539 A | 11/2012 |
| CN | 202801864 U | 3/2013 |
| CN | 103209649 A | 7/2013 |
| CN | 103313681 A | 9/2013 |
| CN | 103598902 A | 2/2014 |
| CN | 103945775 A | 7/2014 |
| CN | 104168839 A | 11/2014 |
| CN | 104244843 A | 12/2014 |
| CN | 104519838 A | 4/2015 |
| CN | 104968284 A | 10/2015 |
| CN | 106413586 A | 2/2017 |
| DE | 10148185 A1 | 4/2003 |
| EP | 0991375 B1 | 9/2004 |
| EP | 1790297 A1 | 5/2007 |
| EP | 1480565 B1 | 12/2008 |
| EP | 2543323 A1 | 1/2013 |
| EP | 3136982 A2 | 3/2017 |
| EP | 3136984 A1 | 3/2017 |
| GB | 2409978 A | 7/2005 |
| JP | 2000-505316 A | 5/2000 |
| JP | 2001-501493 A | 2/2001 |
| JP | 2001-520908 A | 11/2001 |
| JP | 2001-340346 A | 12/2001 |
| JP | 2003-527939 A | 9/2003 |
| JP | 2004-049806 A | 2/2004 |
| JP | 2005-503881 A | 2/2005 |
| JP | 2005-518863 A | 6/2005 |
| JP | 2005-528181 A | 9/2005 |
| JP | 2005-534390 A | 11/2005 |
| JP | 2006-006648 A | 1/2006 |
| JP | 2007-530128 A | 11/2007 |
| JP | 2009-508641 A | 3/2009 |
| JP | 2009-518149 A | 5/2009 |
| JP | 2010-523209 A | 7/2010 |
| JP | 2010-528821 A | 8/2010 |
| JP | 2011-509758 A | 3/2011 |
| JP | 2011-519709 A | 7/2011 |
| JP | 2013-013715 A | 1/2013 |
| JP | 2014-503246 A | 2/2014 |
| JP | 2015-500665 A | 1/2015 |
| JP | 2021-155586 A | 10/2021 |
| WO | 97/27898 A1 | 8/1997 |
| WO | 97/32543 A1 | 9/1997 |
| WO | 98/02099 A1 | 1/1998 |
| WO | 98/08462 A2 | 3/1998 |
| WO | 98/16174 A1 | 4/1998 |
| WO | 98/58600 A1 | 12/1998 |

(56) References Cited

FOREIGN PATENT DOCUMENTS

| WO | 01/72367 A1 | 10/2001 |
|---|---|---|
| WO | 2003/028522 A2 | 4/2003 |
| WO | 03/73944 A1 | 9/2003 |
| WO | 2003/103476 A2 | 12/2003 |
| WO | 2004/012603 A2 | 2/2004 |
| WO | 2004/087236 A2 | 10/2004 |
| WO | 2005/089655 A1 | 9/2005 |
| WO | 2006/121855 A2 | 11/2006 |
| WO | 2007/024964 A1 | 3/2007 |
| WO | 2007/053243 A2 | 5/2007 |
| WO | 2007/100970 A2 | 9/2007 |
| WO | 2008/124314 A1 | 10/2008 |
| WO | 2008/157172 A1 | 12/2008 |
| WO | 2009/082718 A1 | 7/2009 |
| WO | 2009/091899 A2 | 7/2009 |
| WO | 2009/109348 A1 | 9/2009 |
| WO | 2009/140195 A1 | 11/2009 |
| WO | 2009/146369 A1 | 12/2009 |
| WO | 2010/129162 A1 | 11/2010 |
| WO | 2012/034108 A1 | 3/2012 |
| WO | 2012/067912 A1 | 5/2012 |
| WO | 2012/071075 A1 | 5/2012 |
| WO | 2013/152891 A2 | 10/2013 |
| WO | 2015/168501 A2 | 11/2015 |
| WO | 2015/168504 A2 | 11/2015 |
| WO | 2015/168506 A1 | 11/2015 |
| WO | 2015/168507 A1 | 11/2015 |
| WO | 2015/168508 A2 | 11/2015 |

\* cited by examiner

ANASTOMOSIS DEVICES

CROSS-REFERENCE TO RELATED APPLICATION

This application is a continuation of U.S. Patent Application is a continuation U.S. patent application Ser. No. 17/039,569, filed Sep. 30, 2020, which is a continuation of U.S. patent application Ser. No. 15/969,038, filed May 2, 2018, now U.S. Pat. No. 10,806,458, issued Oct. 20, 2020, which is a continuation of U.S. patent application Ser. No. 14/700,480, filed Apr. 30, 2015, now U.S. Pat. No. 10,004,509, issued Jun. 26, 2018, which claims the benefit of U.S. Provisional Application 61/987,954, filed May 2, 2014, which are incorporated herein by reference in their entireties for all purposes.

FIELD

The present disclosure relates to implantable medical devices, and more specifically, to implantable devices for connecting tissue layers to create an anastomosis.

BACKGROUND

An anastomosis is a cross-connection between two tissue structures, such as blood vessels or intestines. For example, in the context of coronary artery bypass graft surgery, a graft vessel is anastomosed to a native coronary artery so that blood can flow through the graft vessel.

Anastomoses can be created in various manners including, but not limited to: end-to-end, end-to-side, and side-to-side anastomoses. Often, suturing is used to create such anastomoses.

SUMMARY

A first aspect of the invention relates to an implantable medical device that includes (1) a first apposition portion having a plurality of first apposition members, (2) a second apposition portion having a plurality of second apposition members, and (3) a central portion having at least one supported region and at least one unsupported region. The supported region includes a frame member and the unsupported region includes a covering material. The central portion interconnects the first and second apposition portions and is selectively longitudinally contractible. In some embodiments, the first apposition portion and the supported region includes a first elongate member and the second apposition portion includes a second elongate member. The unsupported region may consist of the cover material. In some embodiments, the first elongate member has a first stiffness and/or a first geometry and the second elongate member has a second stiffness and/or a second geometry that is different than the first stiffness and/or first geometry, respectively. In at least one embodiment, the first apposition portion, the supported region, and the second apposition member is formed of a single elongate member. The device may also include a tether affixed to one of the first apposition portion and the second apposition portion. The device may further include at least one locking member. In some embodiments, the collapsible central portion includes an unsupported region positioned between a first supported region and a second supported region.

A second aspect of the invention relates to an implantable medical device that includes (1) a first apposition portion, (2) a second apposition portion, (3) a collapsible central portion interconnecting the first and second apposition members, and (4) a tether to collapse the central portion. The device optionally includes at least one locking member. The central portion has therein at least one unsupported region that includes a cover material. In at least one exemplary embodiment, the first apposition portion includes a first elongate member and the second apposition portion includes a second elongate member. The first elongate member may have a first geometry and/or first stiffness and the second elongate member has a second geometry and/or second stiffness that is different than the first geometry and/or second stiffness. In addition, the first apposition portion and the second apposition portion may be formed of a single elongate member.

A third aspect of the invention relates to a method for creating an anastomosis that includes (1) positioning a medical device in an undeployed configuration such that the medical device spans a first body part and a second body part and (2) providing a hollow conduit therebetween. The implantable medical device includes (1) a first apposition portion, (2) a second apposition portion, (3) a collapsible central portion having at least one supported region and an unsupported region, and (4) a tether affixed to one of the first apposition portion and the second apposition portion. Optionally, the device further includes at least one locking member. The central portion interconnects the first and second apposition portions. Also, the supported region includes a frame member and the unsupported region includes a covering material. The method further includes applying a force to the tether to draw the first apposition portion and the second apposition portion towards each other and collapse the central portion to place the medical device in a deployed configuration, the deployed configuration having a shortened length relative to the undeployed configuration.

DESCRIPTION OF DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1:
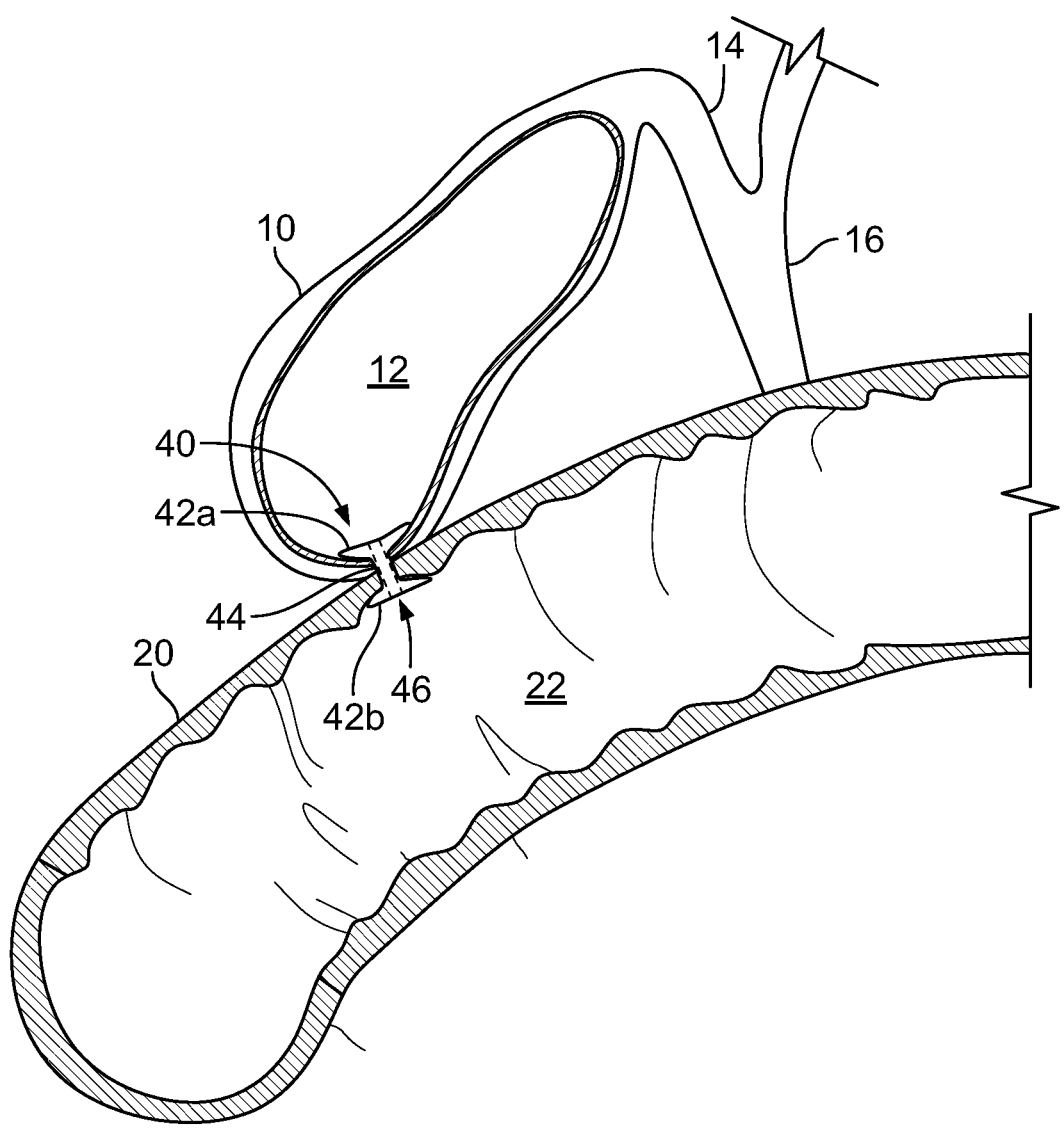
FIG. 1 is a cutaway perspective view of an exemplary stent device that has been implanted within a patient to act as a shunt between the patient's gallbladder and intestine in accordance with some embodiments.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The present disclosure is directed to implantable devices for connecting tissue layers, for example, to circumvent a conduit or organ blockage, such as by creating a direct passage between tissue structures (e.g. connecting a gallbladder and a portion of a gastrointestinal tract) to create an anastomosis that facilitates material flow therebetween. The devices described herein are endoscopically deployable or deliverable via a catheter and may include self-expanding apposition mechanisms that facilitate a secure connection between the tissue structures (such a connection may also be referred to herein as a "shunt," "passageway," "shunt passageway," or "tunnel"). Such design features simplify implantation and reduce the likelihood of complications. In some embodiments, the devices provided herein are configured to be removable after implantation. As one example, the device is implanted and remains in place until the gallbladder and/or its associated ducts are cleared of blockages, after which the device is removed. In another example, the device remains implanted until the body grows a tissue-anastomosis around the device, and then the device is removed. In other embodiments, tissue ingrowth into and/or around the device permanently implants the device, and the device is not removed.

The devices described herein can provide alternative treatments for patients who are not suitable candidates for other types of treatments (e.g., gallbladder removal surgery) and/or to avoid known complications of other types of treatments (e.g., external biliary drainage).

This disclosure refers to anastomosis devices in an exemplary fashion. That is, it should be understood that the inventive concepts disclosed in this disclosure can also be applied to other types of devices. For example, this disclosure also provides implantable devices that, in some embodiments, can be used for occluding tissue structures, organs, body conduits, blood vessels, the GI tract, and the like. For example, in some embodiments the devices provided herein can be used to occlude septal defects. In some embodiments, the devices provided herein can be used to occlude a patient's vasculature or GI tract. In some such embodiments, the device does not include a tunnel or central aperture through the device. Rather, in some embodiments a covering material seals the device to inhibit, modulate, or substantially prevent material from flowing through the device.

Referring to FIG. 1, an exemplary anastomosis device 40 in accordance with some embodiments provided herein that can be implanted in a patient to create a fluidic connection between two organs, spaces, tissue structures, conduits, and the like, and combinations thereof is depicted. For example, in the depicted implementation the anastomosis device 40 is connecting a gallbladder 10 (that defines an internal gallbladder space 12) with an intestine 20 (that defines an internal intestinal space 22). Hence, the anastomosis device 40 is acting as a fluidic shunt device between the internal gallbladder space 12 and the internal intestinal space 22. Such an implementation may provide a beneficial treatment to the patient when, for example, a flow blockage exists in the native anatomical conduits connecting the internal gallbladder space 12 and the internal intestinal space 22. For example, in some instances the patient may have one or more gallstones that cause a blockage of the patient's cystic duct 14 and/or common bile duct 16. In such a case, the anastomosis device 40 can provide a fluidic passageway such that bile from the gallbladder 10 can flow into the intestine 20. If not for the anastomosis device 40, when bile is blocked from flowing out of the gallbladder 10 cholecystitis (inflammation of the gallbladder 10) may result.

While the anastomosis devices provided herein can be used in some implementations to relieve or prevent cholecystitis as described above, it should be understood that the anastomosis devices provided herein can also be used in many other types of implementations within a patient. For example, the anastomosis devices provided herein can be used in conjunction with various body tissue structures and organs such as, but not limited to, stomachs, colons, small intestines, pancreases, blood vessels, bladders, kidneys, conduits, and the like.

In general, some embodiments of the anastomosis devices provided herein (of which anastomosis device 40 is one type of example), include a first tissue apposition portion 42a, a second tissue apposition portion 42b, and a central portion 44 therebetween. The central portion 44 defines a lumen 46 that extends longitudinally from a first end of the anastomosis device 40 to a second end of the device 40. The lumen 46 acts as a connection (e.g., a shunt, or passageway) between the internal gallbladder space 12 and the internal intestinal space 22, such that the internal gallbladder space 12 is in fluid communication with the internal intestinal space 22 via the anastomosis device 40. The lumen 46 has a radial (circular) rigidity by which the anastomosis device 40 remains patent.

It should be understood that one or more design features of the anastomosis devices provided herein can be combined with one or more other features of other anastomosis devices provided herein. In effect, hybrid designs that combine various features from two or more of the anastomosis device designs provided herein can be created, and are considered to be within the scope of this disclosure.

Figure 2:
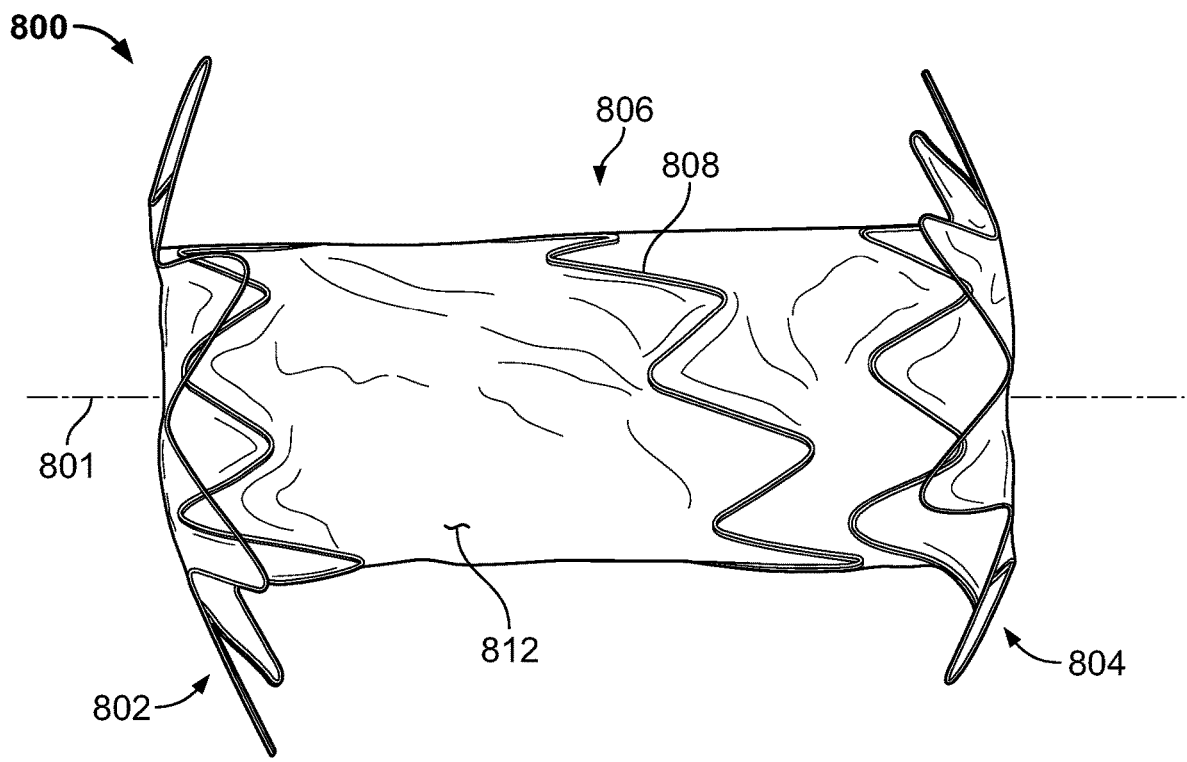
FIG. 2 is a side view an exemplary anastomosis device in accordance with some embodiments.
Figure 3:
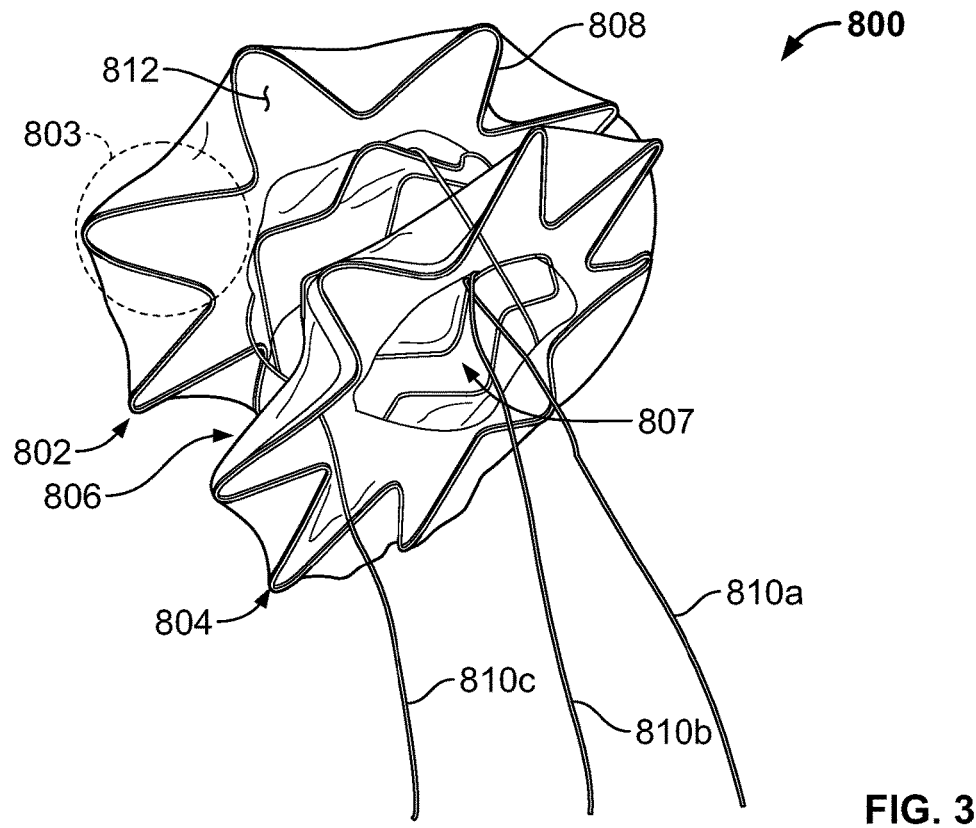
FIG. 3 is a perspective view of the anastomosis device of FIG. 2 shown in a longitudinally contracted configuration.
Figure 4:
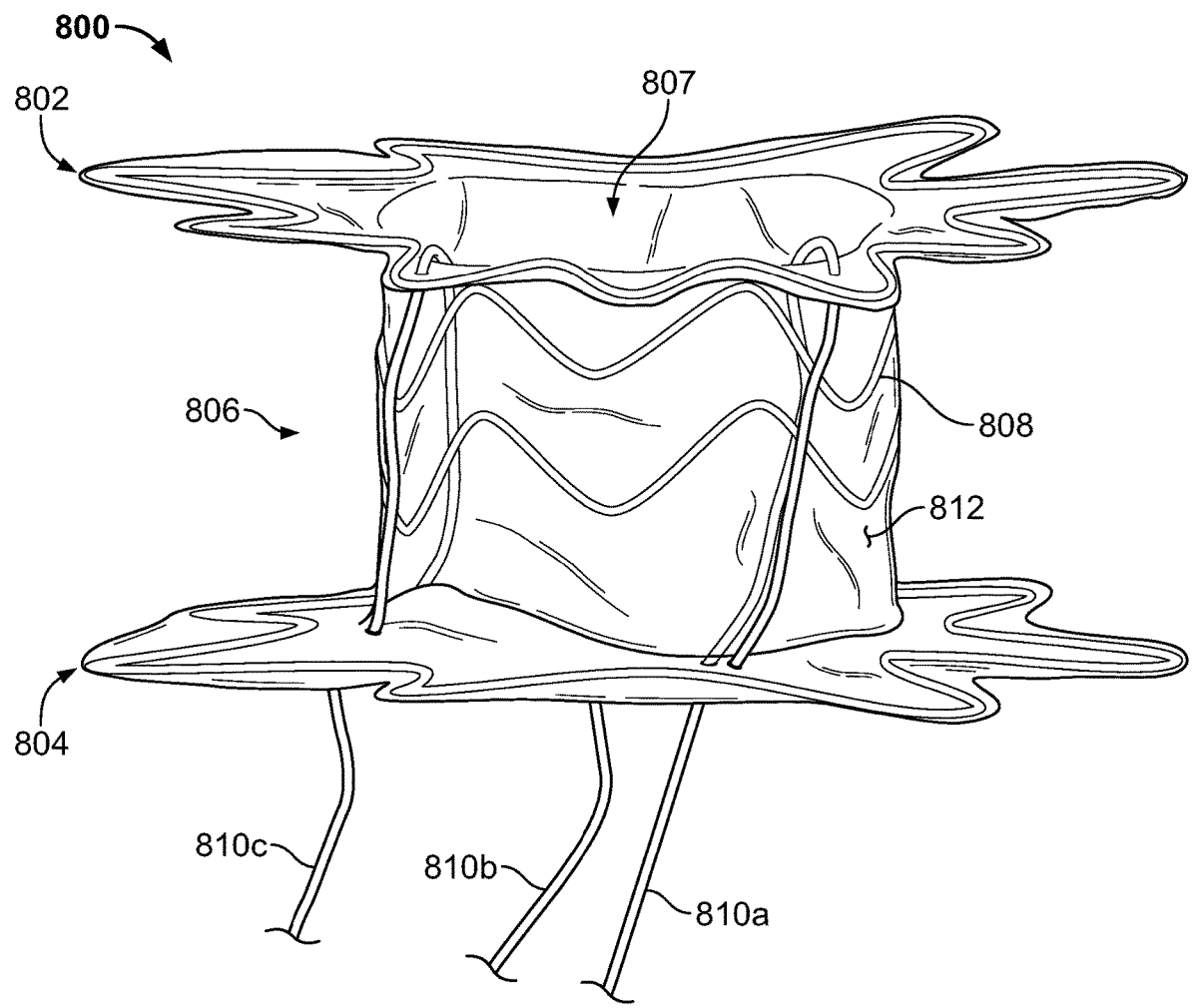
FIG. 4 is a side view of the anastomosis device of FIG. 2 shown in a longitudinally contracted configuration.

Referring to FIGS. 2-4, an exemplary anastomosis device 800 includes a framework of one or more elongate elements 808 that defines a first apposition portion 802, a second apposition portion 804, and a central portion 806. The anastomosis device 800 defines a longitudinal axis 801. The central portion 806 is disposed between and interconnects the first apposition portion 802 and the second apposition portion 804. In some embodiments, a covering material 812 is disposed on at least some portions of the framework.

The example anastomosis device 800 also includes a first tether 810a, a second tether 810b, and a third tether 810c. As described further below, in some embodiments the tethers 810a, 810b, and 810c are used to longitudinally contract the anastomosis device 800 in situ. While the depicted embodiment includes three tethers 810a, 810b, and 810c, in some embodiments less than three or more than three tethers are included. For example, in some embodiments one tether, two tethers, or more than three tethers are included.

In some embodiments, a covering material 812 is disposed on at least some portions of the anastomosis device 800. As described further below, the covering material 812 can be disposed on some portions or on all of the first apposition portion 802, the second apposition portion 804, and/or the central portion 806. In some embodiments, portions of the first apposition portion 802, the second apposition portion 804, and/or the central portion 806 can remain free of the covering material 812.

In some embodiments, the central portion 806 defines a lumen 807 that extends between the first apposition portion 802 and the second apposition portion 804. In some implementations, the lumen 807 provides a passageway through which biological materials or liquids can pass. The anastomosis device 800 is shown in an expanded configuration (also referred to herein as a deployed configuration). The expanded or deployed configuration is the configuration that the device 800 naturally exhibits in the absence of external forces acting upon the device 800 (e.g., the forces from being radially constrained in a delivery lumen). In should be understood that when the anastomosis device 800 is implanted in a patient, the configuration of the device 800 may be somewhat different than shown because of the external forces from the patient's anatomy that are exerted on the device 800.

In some embodiments, the framework of the anastomosis device 800, as described further below, can be made of a variety of metallic shape memory materials and/or super-elastic alloys. Thus, in some embodiments the central portion 806 (and/or the apposition portions 802 and 804) can be configured to self-expand to the deployed configuration. In some embodiments, the central portion 806 is balloon expandable to the deployed configuration, or supplemental expansion forces can be applied to a self-expandable device by balloon dilation. The diameter of the central portion 806 can be made in any size as desired in order to suit the intended use and/or delivery system of the anastomosis device 800.

When the anastomosis device 800 is configured in its expanded deployed configuration as shown, the diameter of the central portion 806 increases to a deployed diameter. The diameter of the central portion 806 can be made in any dimension as desired in order to suit the intended use and/or delivery system of the anastomosis device 800. In some implementations, the deployed outer diameter of the central portion 806 is configured to at least partially anchor the device 800 via an interference fit with the tissue aperture in which the central portion 806 resides. However, in some implementations the deployed outer diameter of the central portion 806 is slightly less than the diameter of the tissue aperture in which the central portion 806 resides, and the apposition portions 802 and 804 compress the tissue to provide the migration resistance. In some embodiments, the fully expanded diameter of the central portion 806 is about 30 mm, or about 25 mm, or about 20 mm, or about 15 mm, or about 12 mm, or about 10 mm, or about 8 mm, or about 6 mm, or about 4 mm, and the like. In some embodiments, the fully expanded diameter of the central portion 806 is in a range between about 20 mm to about 30 mm, or about 15 mm to about 25 mm, or about 10 mm to about 20 mm, or about 5 mm to about 15 mm, or about 4 mm to about 8 mm, and the like.

The length of the central portion 806 can be made in any dimension as desired in order to suit the intended use and/or delivery system of the anastomosis device 800. For instance, in one exemplary embodiment the fully longitudinally expanded central portion 806 is about 50 mm in length. In some embodiments, the length of the central portion 806 can be in a range from about 40 mm to about 70 mm, or about 30 mm to about 60 mm, or about 20 mm to about 50 mm, or about 10 mm to about 40 mm, or about 20 mm to about 40 mm.

In some embodiments, the anastomosis device 800 has a framework that comprises one or more elongate elements 808. In some embodiments, the one or more elongate elements 808 are wound into the framework configuration. In some embodiments, a single elongate element 808 is wound to form the framework of the anastomosis device 800. In some embodiments, two or more elongate elements 808 are cooperatively wound to form the framework of the anastomosis device 800.

In some embodiments, the framework of the first apposition portion 802, the second apposition portion 804, and the central portion 806 are formed of one or more elongate elements 808 made of materials such as, but not limited to, spring wire (e.g., L605 steel or stainless steels), shape memory alloy wire (e.g., nitinol or nitinol alloys), super-elastic alloy wire (e.g., nitinol or nitinol alloys), other suitable types of elongate elements or wires, or combinations thereof. In some embodiments, the first apposition portion 802, the second apposition portion 804, and the central portion 806 are formed from a precursor material that is cut to create the framework of elongate elements 808. In some such embodiments, the precursor material is a single piece of precursor material. In some embodiments, one or more elongate elements 808 are wound into a configuration to form the framework. In some embodiments, different types of elongate elements 808 are used at different locations of the first apposition portion 802, the second apposition portion 804, and/or the central portion 806. In some embodiments, the elongate elements 808 of the first apposition portion 802, the second apposition portion 804, and/or the central portion 806 (or portions thereof) may be constructed of polymeric materials.

Suitable materials for the elongate elements 808 of the anastomosis device 800 and/or other devices provided herein include a variety of metallic materials including alloys exhibiting, shape memory, elastic and super-elastic characteristics. Shape memory refers to the ability of a material to revert to an originally memorized shape after plastic deformation by heating above a critical temperature. Elasticity is the ability of a material to deform under load and return (or substantially return) to its original shape when the load is released. Most metals will deform elastically up to a small amount of strain. Super-elasticity refers to the ability of a material to deform under strain to much larger degree than typical elastic alloys, without having this deformation become permanent. For example, the super-elastic materials included in the frames of some anastomosis device embodiments provided herein are able to withstand a significant amount of bending and flexing and then return to or substantially to the frame's original form without deformation.

In some embodiments, suitable elastic materials include various stainless steels which have been physically, chemically, and otherwise treated to produce a high springiness, metal alloys such as cobalt chrome alloys (e.g., ELGILOY™, MP35N, L605), platinum/tungsten alloys. Embodiments of shape memory and super-elastic alloys include the NiTi alloys, ternary shape memory alloys such as NiTiPt, NiTiCo, NiTiCr, or other shape memory alloys such as copper-based shape memory alloys. Additional materials could combine both shape memory and elastic alloys such as drawn filled tube where the outer layer is constructed of nitinol and the inner core is a radiopaque material such as platinum or tantalum. In this construct, the outer layer provides the super-elastic properties and the inner core remains elastic due to lower bending stresses.

In some embodiments, the elongate elements 808 used to construct the anastomosis device 800 and/or other devices provided herein can be treated in various ways to increase the radiopacity of the devices for enhanced radiographic visualization. In some embodiments, the devices are least partially a drawn-filled type of NiTi containing a different material at the core, such as a material with enhanced radiopacity. In some embodiments, the devices include a radiopaque cladding or plating on at least portions of the first apposition portion, the second apposition portion, and the central portion. In some embodiments, one or more radiopaque markers are attached to the devices. In some embodiments, the elongate elements and/or other portions of the devices provided herein are also visible via ultrasound, and may include portions with enhanced echogenicity.

In some embodiments, the materials and configuration of the anastomosis device 800 (and the other anastomosis device embodiments provided herein) allow the devices to be elastically crushed, folded, and/or collapsed into a low-profile delivery configuration for containment within a lumen for transcatheter or endoscopic/thorascopic delivery, and to self-expand to an operative size and configuration once positioned at a desired target site within a body and deployed from the lumen. For example, in the low-profile delivery configuration the anastomosis device 800 can be disposed within a delivery sheath that has about a 15 Fr. (5 mm) outer diameter. However, in some embodiments, sheaths that are smaller or larger than 15 Fr. can be used. For example, sheaths that have outer diameters of 6 Fr., 7 Fr., 8 Fr., 9 Fr., 10 Fr., 11 Fr., 12 Fr., 13 Fr., 14 Fr., 16 Fr., 17 Fr., 18 Fr., 19 Fr., 20 Fr., and larger than 20 Fr., can be used in some embodiments. While the anastomosis device 800 is configured in a collapsed delivery configuration, in some embodiments the framework of one or more elongate elements 808 is radially compressed such that the elongate elements 808 are forced to extend substantially parallel to axis of the central portion 806, and the diameter of the central portion 806 is crushed to become smaller.

The anastomosis device 800 also includes the covering material 812 (which may also be referred to herein as a "covering"). In some embodiments, the covering material 812 is disposed on at least some portions (or on all) of the first apposition portion 802, the second apposition portion 804, and the central portion 806. In some embodiments, some portions of the first apposition portion 802, the second apposition portion 804, and/or the central portion 806 are not covered by the covering material 812.

In some embodiments, the covering material 812 is generally fluid impermeable. That is, in some embodiments the covering material 812 is made of a material that inhibits or reduces passage of blood, bile and/or other bodily fluids and materials through the covering material 812 itself. In some embodiments, the covering material 812 has a material composition and configuration that inhibits or prevents tissue ingrowth and/or endothelialization or epithelialization into the covering material 812. Some such embodiments that are configured to inhibit or prevent tissue ingrowth and/or endothelialization can be more readily removed from the patient at a future date if so desired. In some embodiments, the covering material 812, or portions thereof, has a microporous structure that provides a tissue ingrowth scaffold for durable sealing and/or supplemental anchoring strength of the anastomosis device 800.

In some embodiments, the covering material 812 comprises a fluoropolymer, such as an expanded polytetrafluoroethylene (ePTFE) polymer, or polyvinylidene fluoride (PVDF). In some embodiments, the covering material 812 comprises a polyester, a silicone, a urethane, biocompatible polymer(s), polyethylene terephthalate (e.g., Dacron®), bioabsorbable materials, copolymers, or combinations thereof. In some embodiments, the covering material 812 comprises a bioabsorbable web. In other embodiments, the bioabsorbable material may also provide an anti-migration feature by promoting attachment between the device 800 and tissue until the bioabsorbable material is absorbed.

In some embodiments, the covering material 812 (or portions thereof) is modified by one or more chemical or physical processes that enhance one or more properties of the material 812. For example, in some embodiments, a hydrophilic coating may be applied to the covering material 812 to improve the wettability and echo translucency of the material 812. In some embodiments, the covering material 812, or portions thereof, may be modified with chemical moieties that facilitate one or more of endothelial cell attachment, endothelial cell migration, endothelial cell proliferation, and resistance to or promotion of thrombosis. In some embodiments, the covering material 812, or portions thereof, may be modified to resist biofouling. In some embodiments, the covering material 812, or portions thereof, may be modified with one or more covalently attached drug substances (e.g., heparin, antibiotics, and the like) or impregnated with the one or more drug substances.

The drug substances can be released in situ to promote healing, reduce tissue inflammation, reduce or inhibit infections, and to promote various other therapeutic treatments and outcomes. In some embodiments, the drug substance may be, but is not limited to a corticosteroid, a human growth factor, an anti-mitotic agent, an antithrombotic agent, a stem cell material, or dexamethasone sodium phosphate. In some embodiments, a pharmacological agent is delivered separately from the covering material 812 to the target site to promote tissue healing or tissue growth.

Coatings and treatments may be applied to the covering material 812 before or after the covering material 812 is joined or disposed on or around the framework of the anastomosis device 800. Additionally, one or both sides of the covering material 812, or portions thereof, may be coated. In some embodiments, certain coatings and/or treatments are applied to the covering material(s) 812 located on some portions of the anastomosis device 800, and other coatings and/or treatments are applied to the material(s) 812 located on other portions of the anastomosis device 800. In some embodiments, a combination of multiple coatings and/or treatments are applied to the covering material 812, or portions thereof. In some embodiments, certain portions of the covering material 812 are left uncoated and/or untreated. In some embodiments, the device 800 is fully or partially coated to facilitate or frustrate a biological reaction, such as, but not limited to, endothelial cell attachment, endothelial cell migration, endothelial cell proliferation, and resistance to or promotion of thrombosis.

In some embodiments, a first portion of the covering material 812 is formed of a first material and a second portion of the covering material 812 is formed of a second material that is different than the first material. In some embodiments, the covering material 812 is comprised of multiple layers of materials, which may be the same or different materials. In some embodiments, portions of the covering material 812 have one or more radiopaque markers attached thereto to enhance in vivo radiographic visualization of the anastomosis device 800, or one or more echogenic areas to enhance ultrasonic visibility.

In some embodiments, one or more portions of the covering material 812 are attached to the framework of the device 800, such as the central portion 806 and/or the apposition portions 802 and 804. The attachment can be accomplished by a variety of techniques such as, but not limited to, stitching the covering material 812 to the framework of the device 800, adhering the covering material 812 to the framework of the device 800, laminating multiple layers of the covering material 812 to encompass portions of the elongate members of the device 800, using clips or barbs, laminating multiple layers of the covering material together through openings in the framework of the device 800. In some embodiments, the covering material 812 is attached to the framework of the device 800 at a series of discrete locations, thereby facilitating the flexibility of the framework. In some embodiments, the covering material 812 is loosely attached to the framework of the device 800. It is to be appreciated that the covering material 812 may be attached to the framework using other techniques or combinations of techniques described herein.

In some embodiments, the framework of the device 800 (or portions thereof) is coated with a bonding agent (e.g., fluorinated ethylene propylene (FEP) or other suitable adhesive) to facilitate attachment of the covering material 812 to the framework. Such adhesives may be applied to the framework using contact coating, powder coating, dip coating, spray coating, or any other appropriate means.

In some embodiments, the covering material 812 can adapt to changes in the length and/or diameter of the central portion 806 in a variety of manners. In a first example, the covering material 812 can be elastic such that the covering material 812 can stretch to accommodate changes in the length and/or diameter of the device 800. In a second example, the covering material can include slackened material in the low-profile delivery configuration that becomes less slackened or totally unslackened when the device 800 is in the expanded configuration. In a third example, the covering material 812 can include folded portions (e.g., pleats) that are folded in the low-profile configuration and less folded or totally unfolded when the device 800 is in the expanded configuration. In some embodiments, combinations of such techniques, and/or other techniques can be used whereby the covering material 812 can adapt to changes in the length and/or diameter of the central portion 806.

The one or more elongate element(s) 808 of the central portion 806 can be configured in various ways to define a generally cylindrical framework. In the embodiment depicted in FIG. 2, the elongate element(s) 808 of the central portion 806 are wound circumferentially around the central portion 806. In addition to the circumferential winding, the elongate element(s) 808 can exhibit other winding paths, such as the wavy or serpentine path shown (e.g., approximately sinusoidal) and other paths. In the depicted embodiment, the winding path of the elongate element(s) 808 in the central portion 806 has about eight apices per circumference. In some embodiments, the elongate element(s) 808 of the central portion 806 can be made to have more or less than eight apices per circumference. For example, in some embodiments the elongate element(s) 808 of the central portion 806 can be made to have three, four, five, six, seven, nine, ten, eleven, twelve, thirteen, fourteen, fifteen, sixteen, or more than sixteen apices per circumference.

It should be understood that, while the anastomosis device 800 is in the expanded configuration, the anastomosis device 800 may be selectively adjusted to a desired longitudinal length by manipulation of the tethers 810a, 810b, and 810c. For example, FIG. 2 shows the anastomosis device 800 configured to have its maximum longitudinal length. In contrast, FIGS. 3 and 4 show the anastomosis device 800 configured to have a shorter longitudinal length. The shorter longitudinal length of the anastomosis device 800 is attained by pulling tethers 810a, 810b, and 810c proximally, to thereby longitudinally compress (contract) the central portion 806. Hence, the central portion 806 of the anastomosis device 800 can be characterized as being selectively longitudinally contractible. In some embodiments, the tethers 810a, 810b, and 810c will lock in their positions such that the longitudinally contracted arrangement of the anastomosis device 800 will be retained.

In some embodiments, the anastomosis device 800 includes a single elongate element 808. That is, in some embodiments a single continuous elongate element 808 forms the framework of each of the first apposition portion 802, the second apposition portion 804, and the central portion 806.

In some embodiments, the anastomosis device 800 includes two elongate elements 808. That is, in some embodiments two elongate elements 808 are used to form the framework of the first apposition portion 802, the second apposition portion 804, and the central portion 806. For example, in some embodiments a first elongate element 808 may form the framework of just the first apposition portion 802, and a second elongate element 808 may form the framework of both of the second apposition portion 804 and the central portion 806. In another example, a first elongate element 808 may form the framework of both of the first apposition portion 802 and the central portion 806, and a second elongate element 808 may form the framework of just the second apposition portion 804.

In some embodiments, the anastomosis device 800 includes three elongate elements 808. That is, in some embodiments a first continuous elongate element 808 forms the framework of the first apposition portion 802, a second elongate element 808 forms the framework of the second apposition portion 804, and a third elongate element 808 forms the framework of the central portion 806. Such a configuration may provide some advantages. For example, having a separate elongate element 808 in the central portion 806 may allow for a smaller low-profile delivery configuration. In addition, a separate elongate element 808 in the central portion 806 may allow for more conformability to tissue topography and allow the central axis 801 to bend to accommodate organ locations and/or peristalsis, generally independent of the first and second apposition portions 802 and 804.

In some embodiments, the anastomosis device 800 includes more than three elongate elements 808. In some embodiments, one or both of the first apposition portion 802 and/or the second apposition portion 804 can be comprised of more than one elongate elements 808.

In some embodiments that include two or more elongate elements 808, the elongate elements 808 may have differing properties, such as, but not limited to, diameters, stiffnesses, material compositions, shape-memory properties, cross-sectional shapes, geometries, elasticities, and the like.

The anastomosis device 800 includes the first apposition portion 802 and the second apposition portion 804. In some embodiments, the configurations (geometries) of the apposition portions 802 and 804 are substantially the same. In some embodiments, the configurations of the apposition portions 802 and 804 are different from each other. For example, in some embodiments the first apposition portion 802 may have multiple apposition members 803 (refer to FIG. 3), while the second apposition portion 804 may have more, fewer, or no apposition members 803. In another example, in some embodiments the first apposition portion 802 may have multiple apposition members 803 shaped generally as shown, while the second apposition portion 804 may have multiple apposition members that are shaped differently. All such combinations and permutations are envisioned, and within the scope of this disclosure.

In some embodiments, such as the depicted embodiment, the elongate element 808 of the central portion 806 is configured in a sinusoidal pattern that is wrapped helically around the longitudinal axis 801 along the central portion 806. In some embodiments, a majority of the central portion 806 is unsupported by the elongate element 808 of the central portion 806. In some embodiments, one or more elongate elements 808 may be configured in any other suitable arrangement in the central portion 806.

In some embodiments, the central portion 806 includes one or more supported regions and one or more unsupported regions. The one or more supported regions are the regions of the central portion 806 where the elongate element 808 is disposed. The one or more unsupported regions are the regions of the central portion 806 where no elongate element 808 is disposed (hence the covering material 812 is unsupported by the elongate element 808 in the unsupported regions).

The anastomosis device 800 includes the tethers 810a, 810b, and 810c. In some embodiments the tethers 810a, 810b, and 810c are used to longitudinally contract the anastomosis device 800 in situ. That is, by pulling on tethers 810a, 810b, and 810c, a clinician can longitudinally shorten the central portion 806 of the anastomosis device 800.

In some embodiments, the tethers 810a, 810b, and 810c are disposed in a range from about 1000 to about 1400 apart from each other, or in a range from about 1100 to about 1300 apart from each other, or at about 1200 apart from each other around the periphery of the anastomosis device 800. In some embodiments, other relative arrangements between the tethers 810a, 810b, and 810c are used. While in the depicted embodiment, the anastomosis device 800 includes three tethers 810a, 810b, and 810c, in some embodiments one, two, four, five, six, seven, eight, nine, ten, or more than ten tethers are included.

In some embodiments, the tethers 810a, 810b, and 810c are made of materials such as, but not limited to, PTFE (polytetrafluoroethylene), nylon, and the like, and combinations thereof. In some embodiments, the tethers 810a, 810b, and 810c are monofilaments. In some embodiments, the tethers 810a, 810b, and 810c are multifilament constructs such as braided or twisted constructs. In some embodiments, it is advantageous for the tethers 810a, 810b, and 810c to have low elasticity to provide a clinician with precision control of the application of contraction forces to the central portion 806.

In some embodiments, the paths of the tethers 810a, 810b, and 810c are generally as follows. The first ends of the tethers 810a, 810b, and 810c are located proximally and exterior to the patient such that the clinician can apply tension to the tethers 810a, 810b, and 810c. From the proximal ends, the tethers 810a, 810b, and 810c extend towards the anastomosis device 800 (e.g., through one or more lumens of a catheter). As shown, the tethers 810a, 810b, and 810c pass through a proximal end (e.g., near apposition portion 804) of the anastomosis device 800 and extend to a distal end (e.g., near apposition portion 802) of the anastomosis device 800. At the distal end of the anastomosis device 800, the tethers 810a, 810b, and 810c are routed through or around a structure of the anastomosis device (e.g., the elongate element 808 or covering material 812) and then back towards the proximal end of the anastomosis device 800. The second ends of the tethers 810a, 810b, and 810c are tied or otherwise affixed to a structure of the anastomosis device 800 at the proximal end of the anastomosis device 800. As a result of being routed in this fashion, when a clinician pulls or applies tension to one or more of the tethers 810a, 810b, and 810c, the central portion 106 of the anastomosis device 800 will be longitudinally compressed.

In some embodiments, locking members are included such that the tethers 810a, 810b, and 810c remain detained (locked) in a tensioned state after the clinician has induced a desired amount of shortening to the central portion 806 by pulling on the tethers 810a, 810b, and 810c.

The anastomosis device 800 can advantageously be used to adapt to a range of tissue thicknesses. Accordingly, the size selection of the anastomosis device 800 for a particular target location is simplified. In the example deployment process depicted in FIGS. 5-8, the anastomosis device 800 is being used to create an anastomosis between two tissue walls 50 and 60.

Figure 5:
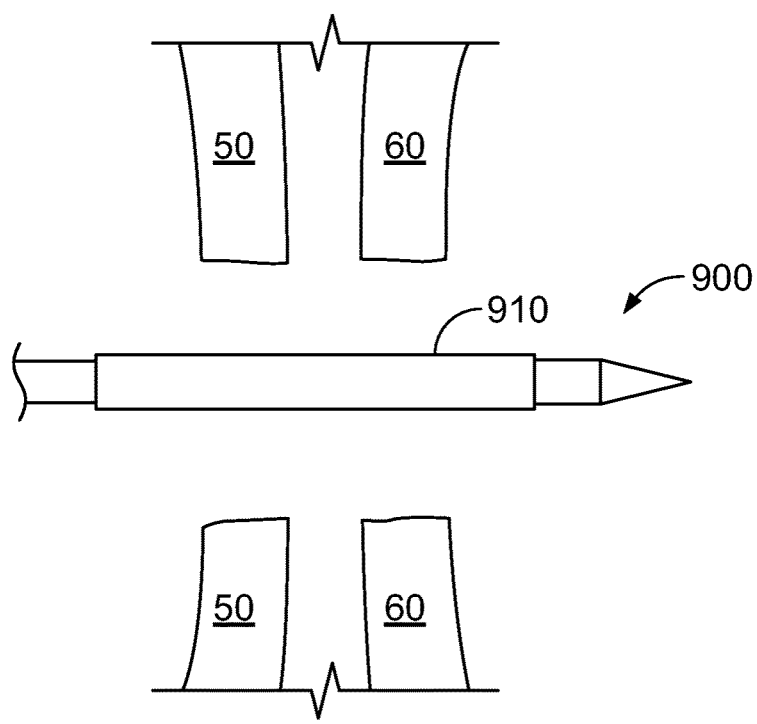
FIGS. 5-8 are a series of schematic illustrations showing the deployment process of the anastomosis device of FIG. 2.

Referring to FIG. 5, a deployment catheter 900 that has been navigated to an opening between the two tissue walls 50 and 60 is shown. The deployment catheter 900 contains the anastomosis device 800 in a radially compressed low-profile delivery configuration. In some implementations, the deployment catheter 900 has been navigated to the opening via an endoscope working channel.

Figure 6:
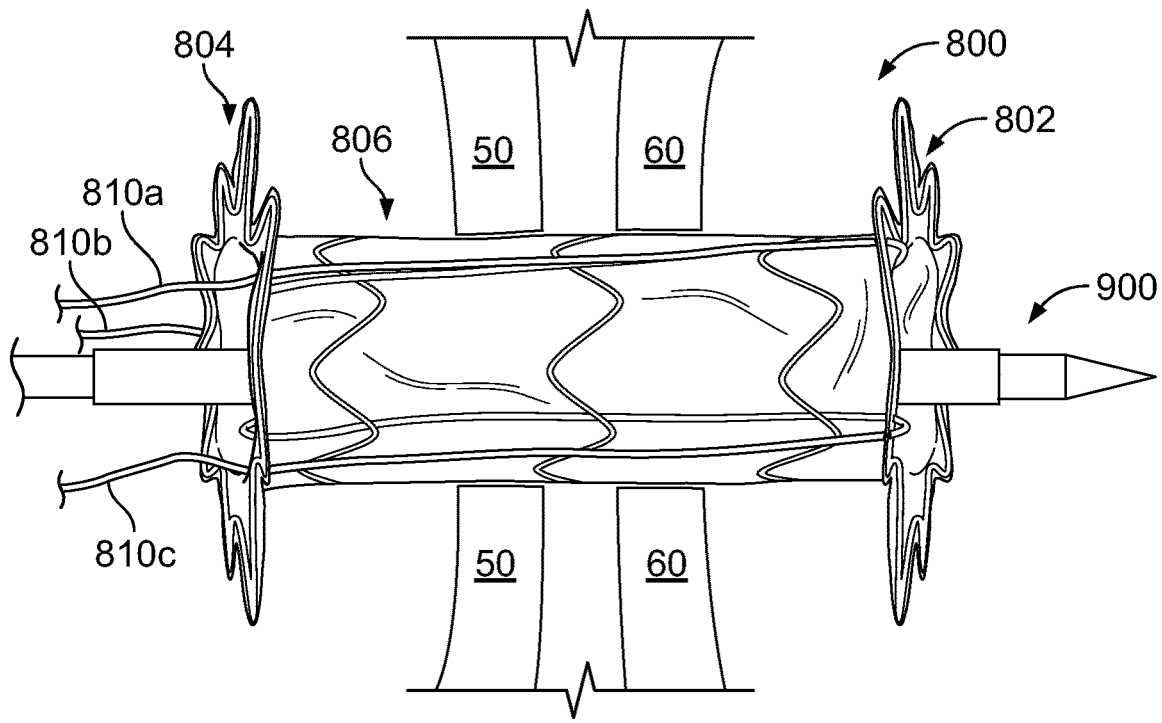

Referring to FIG. 6, the anastomosis device 800 has been deployed from the deployment catheter 900. The anastomosis device 800 has been deployed such that the first apposition portion 802 and the second apposition portion 804 are on opposite sides of the double tissue walls 50 and 60. In some embodiments, the deployment comprises removing an outer containment member from the anastomosis device 800 (such as a polymeric sleeve that can be "unzipped"). In some embodiments, the deployment comprises pushing the anastomosis device 800 out of a lumen. In some embodiments, the deployment comprises pulling back a delivery sheath so that the anastomosis device emerges from a lumen of the delivery sheath.

Initially after deployment from the deployment catheter 900, the anastomosis device 800 is radially expanded and longitudinally expanded. Radially, the anastomosis device 800 conforms to the opening or near to the opening of the tissues 50 and 60. Longitudinally, the anastomosis device 800 is in its full length arrangement.

Figure 7:
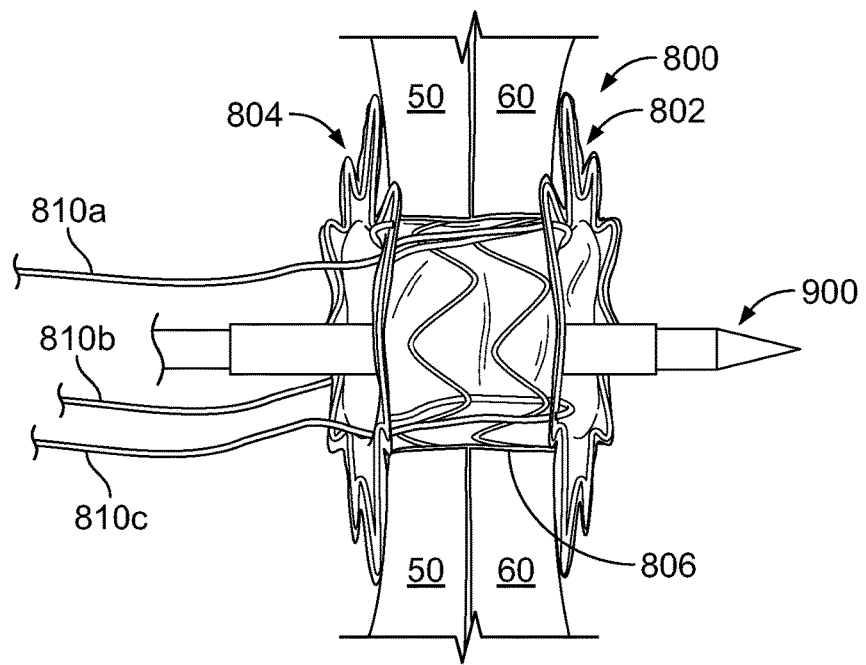

Referring to FIG. 7, a clinician user can apply tension to the tethers 810a, 810b, and 810c to longitudinally shorten (contract) the anastomosis device 800. In doing so, the first apposition portion 802 and the second apposition portion 804 can come into contact with the tissue walls 60 and 50 respectively. In some implementations, the contraction of the anastomosis device 800 may also force the tissue walls 50 and 60 closer together, or into contact with each other.

Figure 8:
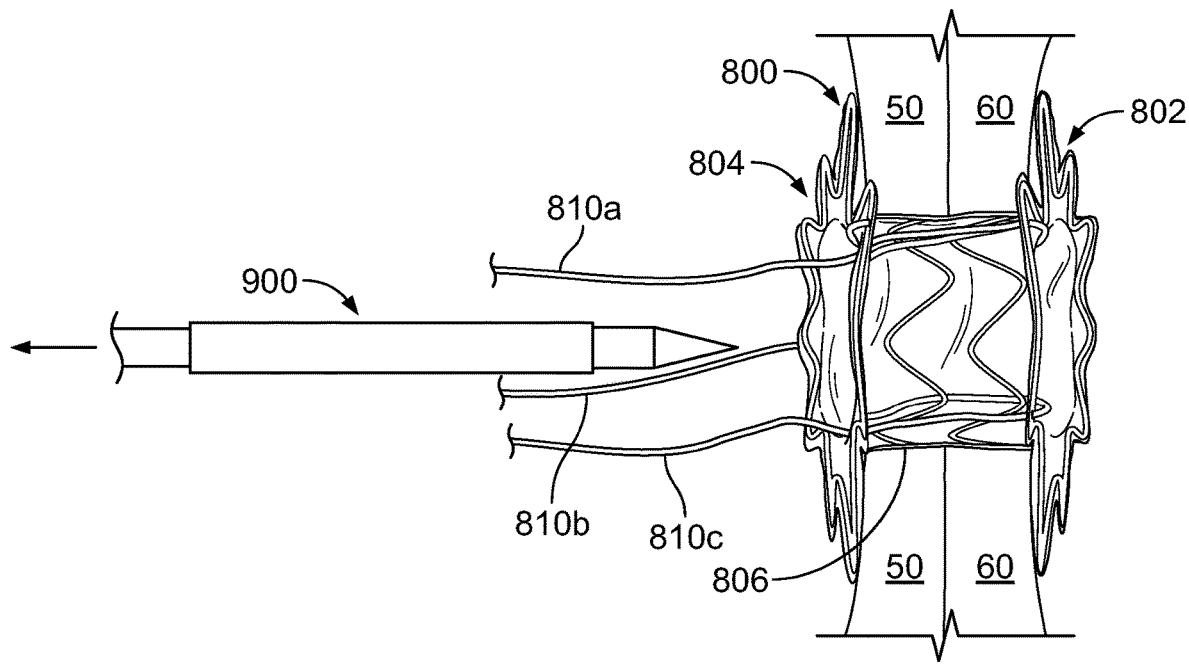

Referring to FIG. 8, the deployment catheter 900 can be withdrawn. In some implementations, the tethers 810a, 810b, and 810c are left attached to the anastomosis device 800 as shown. In some implementations, the tethers 810a, 810b, and 810c are left attached to the anastomosis device 800 but the tethers 810a, 810b, and 810c are trimmed in length. The tethers 810a, 810b, and 810c may be used later to assist with removal of the anastomosis device 800 in some cases.

The anastomosis devices provided herein are deployable to a target site within a patient using one or more catheters, delivery sheaths, and other suitable devices and techniques. In some implementations, the anastomosis devices provided herein are deployable using an endoscopic or laparoscopic approach.

In some embodiments the devices provided herein can be used for sealing or anchoring a heart valve implant. A heart valve implant enables one-way flow of blood from a heart chamber and usually has a first inflow end and a second outflow end. The contractions of the heart cause flow of blood through the valve from the inflow end to the outflow end. Between the inflow and outflow ends, a valve assembly within the heart valve implant provides for one way flow, opening to allow flow from the inflow to the outflow end when the pressure of the blood is higher on the inflow end, and closing to prevent flow when the pressure on the outflow end is higher than the inflow end. In some embodiments, the device includes a tunnel or central aperture through the device with apposition portions to anchor a valve assembly and seal against backward flow. A valve assembly can be attached in the tunnel or central aperture. The apposition portions of the device can be configured to be highly conformable to the topography of the heart chambers or blood vessels, and compliant with the beating movements of the heart. In some embodiments, a covering material is configured to allow flow through a valve assembly in the tunnel or aperture while preventing flow around the apposition portions.

It should be understood that one or more design features of the anastomosis devices provided herein can be combined with other features of other anastomosis devices provided herein. In effect, hybrid designs that combine various features from two or more of the anastomosis device designs provided herein can be created, and are within the scope of this disclosure.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A medical device comprising:
    a framework including one or more elongate members, the framework defining:
        a first apposition portion;
        a second apposition portion; and
        a central portion positioned longitudinal between and interconnecting the first apposition portion and the second apposition portion, wherein the framework central portion comprises only a single elongate member that extends around a circumference of the central portion less than three times helically between the first apposition portion and the second apposition portion;
    a covering material disposed on at least a portion of the framework.

2. The medical device of claim 1, wherein the framework extending around the circumference of the central portion includes a serpentine shape when in an expanded configuration.

3. The medical device of claim 2, wherein the framework extending around the circumference of the central portion includes sections that extend parallel to a longitudinal axis of the central portion when in a radially compressed configuration.

4. The medical device of claim 1, wherein the framework extending around the circumference of the central portion includes about eight apices per circumference.

5. The medical device of claim 1, wherein the framework extending around the circumference of the central portion includes a first elongate member of the one or more elongate members and one of the first and second apposition portions includes a second elongate member of the one or more elongate members.

6. The medical device of claim 5, wherein the first elongate member includes differing properties than the second elongate member.

7. The medical device of claim 6, wherein the differing properties are selected from one of diameter, stiffness, material composition, shape memory property, cross-sectional shape, geometry, and elasticity.

8. The medical device of claim 1, wherein the majority of the covering material at the central portion is unsupported by the single elongate member.

9. The medical device of claim 1, further comprising a tether extending from a first end to longitudinally collapse the central portion.

10. The medical device of claim 9, wherein the tether is routed through the central portion.

11. The medical device of claim 9, wherein the tether is routed through the central portion.

12. The medical device of claim 1, wherein the majority of the covering material at the central portion is unsupported by the one or more elongate members.

13. The medical device of claim 1, further comprising a tether extending from a first end to longitudinally collapse the central portion.

14. A medical device comprising:
    a framework including one or more elongate members, the framework defining:
        a first apposition portion;
        a second apposition portion; and
        a central portion positioned longitudinal between and interconnecting the first apposition portion and the second apposition portion, wherein the framework central portion comprises only a single elongate member extending around a circumference of the central portion helically between the first apposition portion and the second apposition portion and includes a serpentine shape when in an expanded configuration and wherein the framework extending around the circumference of the central portion includes sections that extend parallel to a longitudinal axis of the central portion when in a radially compressed configuration;
    a covering material disposed on at least a portion of the framework.

15. The medical device of claim 14, wherein the framework extending around the circumference of the central portion includes about eight apices per circumference.

16. The medical device of claim 14, wherein the framework extending around the circumference of the central portion includes a first elongate member of the one or more elongate members and one of the first and second apposition portions includes a second elongate member of the one or more elongate members.

17. The medical device of claim 16, wherein the first elongate member includes differing properties than the second elongate member.

18. The medical device of claim 17, wherein the differing properties are selected from one of diameter, stiffness, material composition, shape memory property, cross-sectional shape, geometry, and elasticity.

* * * * *